United States Patent
Somers

(10) Patent No.: US 7,548,075 B2
(45) Date of Patent: Jun. 16, 2009

(54) PROXIMITY SENSOR FOR X-RAY APPARATUS

(75) Inventor: Petrus Lambertus Maria Somers, Eindhoven (NL)

(73) Assignee: Koninklijke Philips Electronics N.V., Eindhoven (NL)

(*) Notice: Subject to any disclaimer, the term of this patent is extended or adjusted under 35 U.S.C. 154(b) by 86 days.

(21) Appl. No.: 11/573,911

(22) PCT Filed: Aug. 26, 2005

(86) PCT No.: PCT/IB2005/052799

§ 371 (c)(1),
(2), (4) Date: Feb. 19, 2007

(87) PCT Pub. No.: WO2006/025003

PCT Pub. Date: Mar. 9, 2006

(65) Prior Publication Data

US 2007/0269012 A1    Nov. 22, 2007

(30) Foreign Application Priority Data

Aug. 31, 2004 (EP) ................... 04104157
Jan. 20, 2005 (EP) ................... 05100338

(51) Int. Cl.
*G01R 27/26* (2006.01)

(52) U.S. Cl. ............... 324/688; 324/662; 324/658; 378/189

(58) Field of Classification Search ........... 324/688
See application file for complete search history.

(56) References Cited

U.S. PATENT DOCUMENTS

| 3,826,979 | A | 7/1974 | Steinmann |
|---|---|---|---|
| 5,801,340 | A | 9/1998 | Peter |
| 5,973,318 | A | 10/1999 | Plesko |
| 6,081,073 | A | 6/2000 | Salam et al. |
| 6,249,130 | B1 | 6/2001 | Greer |
| 7,098,674 | B2* | 8/2006 | Stanley et al. ............... 324/662 |
| 2002/0000960 | A1 | 1/2002 | Yoshihara et al. |
| 2002/0057238 | A1 | 5/2002 | Nitta et al. |
| 2003/0016205 | A1 | 1/2003 | Mawabata et al. |
| 2003/0080755 | A1* | 5/2003 | Kobayashi .................. 324/658 |
| 2003/0122771 | A1 | 7/2003 | Sumiyoshi et al. |
| 2004/0041756 | A1 | 3/2004 | Henmi et al. |

(Continued)

FOREIGN PATENT DOCUMENTS

DE    4006119 A    8/1991

(Continued)

*Primary Examiner*—Timothy J Dole
*Assistant Examiner*—Benjamin M Baldridge

(57) ABSTRACT

A capacitive proximity sensor comprising an emitter electrode (104) capacitively coupled to receive an electrode (102). A first active guard electrode (110), driven by the output of a unity gain amplifier (108), is provided in respect of the receive electrode (102), to shield parts thereof not facing a potential obstacle (122), and a grounded shield (126) is provided in respect of the emitter electrode (104) to shield parts thereof not facing a potential obstacle (122). A second active guard electrode (103) is provided between the emitter and receiver electrodes (104, 102), just behind the cover (106), which is also driven by the output of the amplifier (108). The second active guard electrode (103) acts to block shortened electric field lines (124) between the emitter and receiver electrodes (104, 102), thereby improving accuracy and reliability of the sensor.

10 Claims, 4 Drawing Sheets

U.S. PATENT DOCUMENTS

2006/0097734 A1* 5/2006 Roziere ................ 324/662
2007/0242805 A1* 10/2007 Somers ................ 378/189

FOREIGN PATENT DOCUMENTS

| | | | |
|---|---|---|---|
| DE | 4006119 | A1 | 8/1991 |
| EP | 0518836 | A1 | 12/1992 |
| EP | 0564164 | A1 | 10/1993 |
| EP | 564164 | A1 | 10/1993 |
| EP | 0753438 | A1 | 1/1997 |
| EP | 518836 | A | 8/2003 |
| FR | 2809132 | A1 | 11/2001 |
| GB | 2378344 | A | 2/2003 |
| WO | 03077013 | A | 9/2003 |

* cited by examiner

PROXIMITY SENSOR FOR X-RAY APPARATUS

This invention relates generally to a capacitive proximity sensor for use in, for example, preventing collisions of a motorised swing arm with nearby objects or people.

Referring to FIGS. 1 and 2 of the drawings, a typical X-ray system comprises a swing arm (C-arc or G-arc) 1 supported proximal a patient table 2 by a robotic arm 3. Housed within the swing arm 1, there is provided an X-ray tube 4 and an X-ray detector 5, the X-ray detector 5 being arranged and configured to receive X-rays 6 which have passed through a patient 7 and generate an electrical signal representative of the intensity distribution thereof.

By moving the swing arm 1, the X-ray tube 4 and detector 5 can be placed at any desired location and orientation relative to the patient 7. Movement of the swing arm 1 is driven by one or more motors (not shown), and in order to protect the patient, the operator and/or other objects from collisions with the swing arm, proximity sensors are placed at critical locations A, B, C and D on the arc of the swing arm 1.

A proximity sensor which is commonly used for this application is known as a capacitive proximity sensor that is able to sense any object or person that is capacitive relative to ground and/or can be statically charged. Capacitive proximity sensors use the face or surface of the sensor as one plate of a capacitor, and the surface of a conductive or dielectric target object as the other. The capacitance varies inversely with the distance between capacitor plates in this arrangement, and a certain value can be set to trigger target detection. The sensing principle is based on the measurement of a change in electric field profile. Thus, if the sensor detects an object, the output voltage will change. A control system is employed to control the speed of the swing arm drive motor if the output voltage drops below a certain level, so as to reduce the motor speed and, eventually, stop it to avoid a collision.

Referring to FIG. 3 of the drawings, in more detail, a known capacitive proximity sensor arrangement comprises a 100 kHz sine oscillator 8, which is capacitively coupled to a sense or "receiver" electrode 9, via an emitter electrode 10 and an electric field (denoted by field lines 11) is created which travels from the emitter 10 to the receiver 9. The receiver 9 is connected to an amplifier 12 having a very high input impedance ("approaching infinity") and a very low output impedance. The gain of the amplifier 12 is approximately unity. The receiver electrode 9 is connected to the input of the amplifier 12 and the output of the amplifier 12 is used to drive a guard electrode 13. Thus, the guard electrode 13 is driven by a signal identical to, but electrically isolated from, the signal imposed on the receiver electrode 9, and the capacitance between the guard electrode 13 and ground cancels the capacitance between the receiver electrode 9 and ground, thereby enhancing the sensitivity of the sensor. The guard electrode 13 shields all parts of the receiver electrode 9 which are not facing a potential obstacle, and this guarding method is known as "active guarding" and, by connecting the output of the 1× amplifier to the guard electrode 13, the receiver electrode 9 "sees" its own potential in the direction of the guard electrode 13, so the space surrounding this area is potential free and no electric field will result. A grounded shield 15 is provided in respect of the sides of the emitter electrode 10 not facing a potential obstacle 14. The output of the amplifier 12 is fed to signal conditioning means 16, the output 17 of which is fed to a processing system (not shown).

When there is no grounding object 14 in the proximity of the sensor, the total capacitive coupling between the emitter and receiver electrodes 9, 10 will "land" on the receiver electrode 9, and its potential will rise to a maximum. The measured potential is rectified and sent as a buffered DC voltage to the processing system. When a grounded object 14 approaches the electrode structures, a part of the potential present on the receiver electrode 9 is drawn away to ground, thereby resulting in a decrease in sense potential, and a corresponding decrease in DC output voltage when a grounded object 14 enters the measuring volume. In order to determine the precise location, orientation and direction of travel of a potential obstacle, several sensors are mounted at key locations A, B, C and D within the protective cover 18 of a swing arm.

The construction of the sensor described above results in a structure that is very sensitive to the presence of objects close to the emitter and receiver electrodes 9, 10, and the cover 18 is so close to the electrodes 9, 10 that it causes a shortening of the field lines 11 from emitter 10 to receiver 9. However, with this sensor construction, if an object (such as blood or contrast media) is located very close to the sensor, just between the electrodes 9, 10, this can actually cause a shortening of the field lines 11 between the two electrodes 9, 10, which causes a corresponding sharp rise in the sensor output voltage, sometimes even beyond the level where no object is present, as shown in FIG. 4 which illustrates the potential signal behaviour where, when an object is very close to the sensor just between the two electrodes, the output voltage rises sharply. This is interpreted by the processing system as a fault situation, whereby the sensor cannot be relied upon.

Another problem which affects output sensitivity of the sensor, arises as a result of variations in material characteristics ($\epsilon_r$) due to changes in temperature and humidity. This leads to a variation in the electric field lines from the emitter to receiver electrodes which changes the sensor output without the presence of a moving object in the measuring volume of the sensor. Since the sensor cannot distinguish such changes from the same changes caused by an object moving closer or further away from the sensor, this may result in the swing arm being unnecessarily slowed down or stopped, or in some cases speeded up.

It is therefore an object of the present invention to provide a proximity sensor, in which spurious shortening of the electric field lines is at least reduced, and the reliability and predictability of the sensor behaviour are thereby significantly increased.

In accordance with the present invention, there is provided a proximity sensor, comprising an emitter electrode and a receiver electrode, and means for generating an electric field from said emitter electrode to said receiver electrode, wherein detection of an object in the proximity of the sensor is indicated by a reduction of sensor output voltage, the sensor further comprising an electrically driven guard electrode located between said emitter and receiver electrodes.

Also in accordance with the present invention, there is provided a swing arm for an imaging system, the swing arm comprising a radiation source and detector, and further comprising one or more proximity sensors as defined above.

The present invention extends to an imaging system, comprising a swing arm as defined above, motive means for moving said swing arm to a desired position relative to a subject to be imaged, and means for controlling said motive means according to the output of said one or more sensors.

Beneficially, second electrically driven guard electrode is provided in respect of said receiver electrode, to shield parts thereof not facing a potention object.

Preferably, said receiver electrode is connected to the input of an amplifier, the output of which drives said first and second guard electrodes. The gain of the amplifier is beneficially substantially unity. A grounded shield is beneficially provided in respect of said emitter electrode, to shield parts thereof not facing a potential object.

These and other aspects of the present invention will be apparent from, and elucidated with reference to, the embodiment described herein.

An embodiment of the present invention will now be described by way of example only and with reference to the accompanying drawings, in which.

Figure 5:
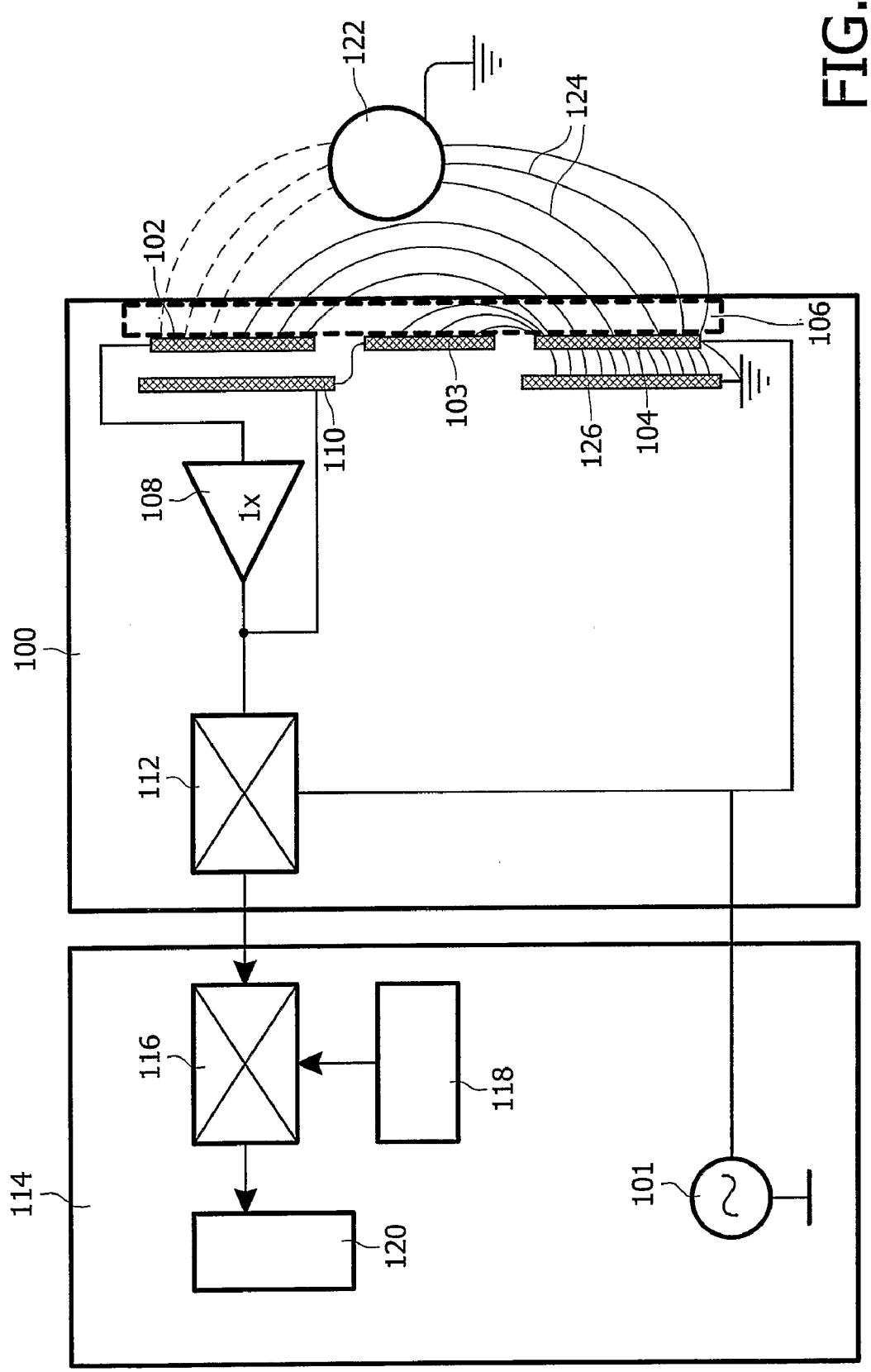
FIG. 5 is a schematic diagram illustrating the principle of construction of a capacitive proximity sensor according to an exemplary embodiment of the present invention.

Referring to FIG. 5 of the drawings, a proximity sensor 100 according to an exemplary embodiment of the present invention comprises a 100 kHz sine oscillator 101 connected to an emitter electrode 104 which is capacitively coupled to a sense or receiver electrode 102, the electrodes 102, 104 being located just behind the cover 106. The receiver electrode 102 is connected to the high impedance input of a unity gain amplifier 108, the low impedance output of which drives an active guard electrode 110 provided in respect of the receiver electrode 102. The amplifier output is also fed to first signal conditioning means 112. A grounded shield 126 is provided in respect of the sides of the emitter electrode 104 not facing a potential obstacle 122. A second electrically driven active guard 103 is provided between the receiver and emitter electrodes 102, 104 just behind the cover 106, as shown in FIG. 5. The second active guard electrode 103 is also driven by the output of the amplifier 108. The potential on the active guard 103 and the sense electrode 102 is ideally the same because if they are different, the sense or receiver electrode 102 sees a capacitive load.

Figure 1:
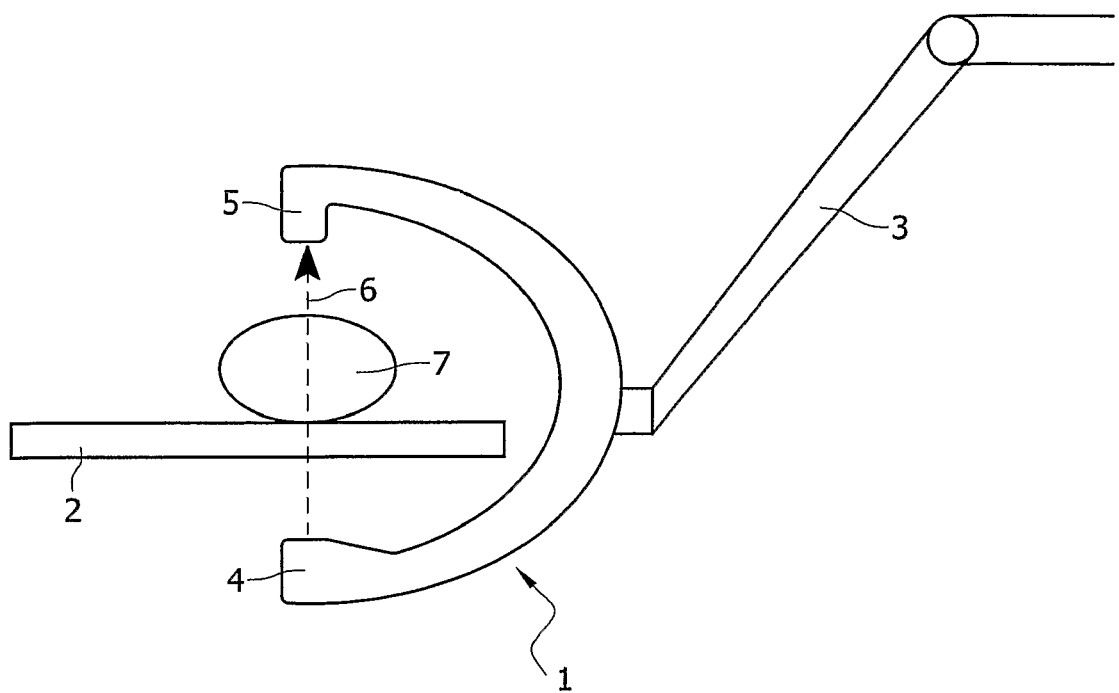
FIG. 1 is a schematic side view of an X-ray swing arm.
Figure 2:
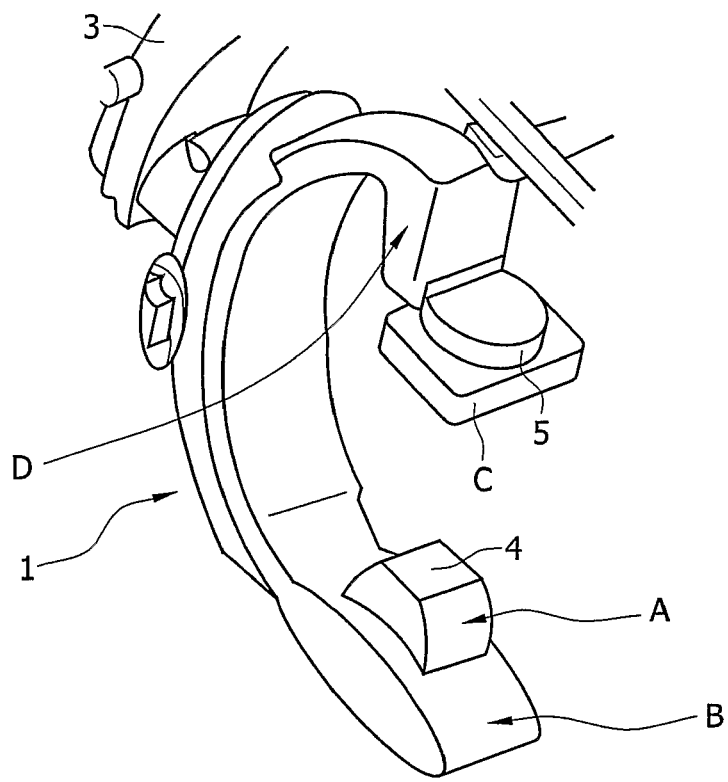
FIG. 2 is a perspective view of an X-ray swing arm.
Figure 3:
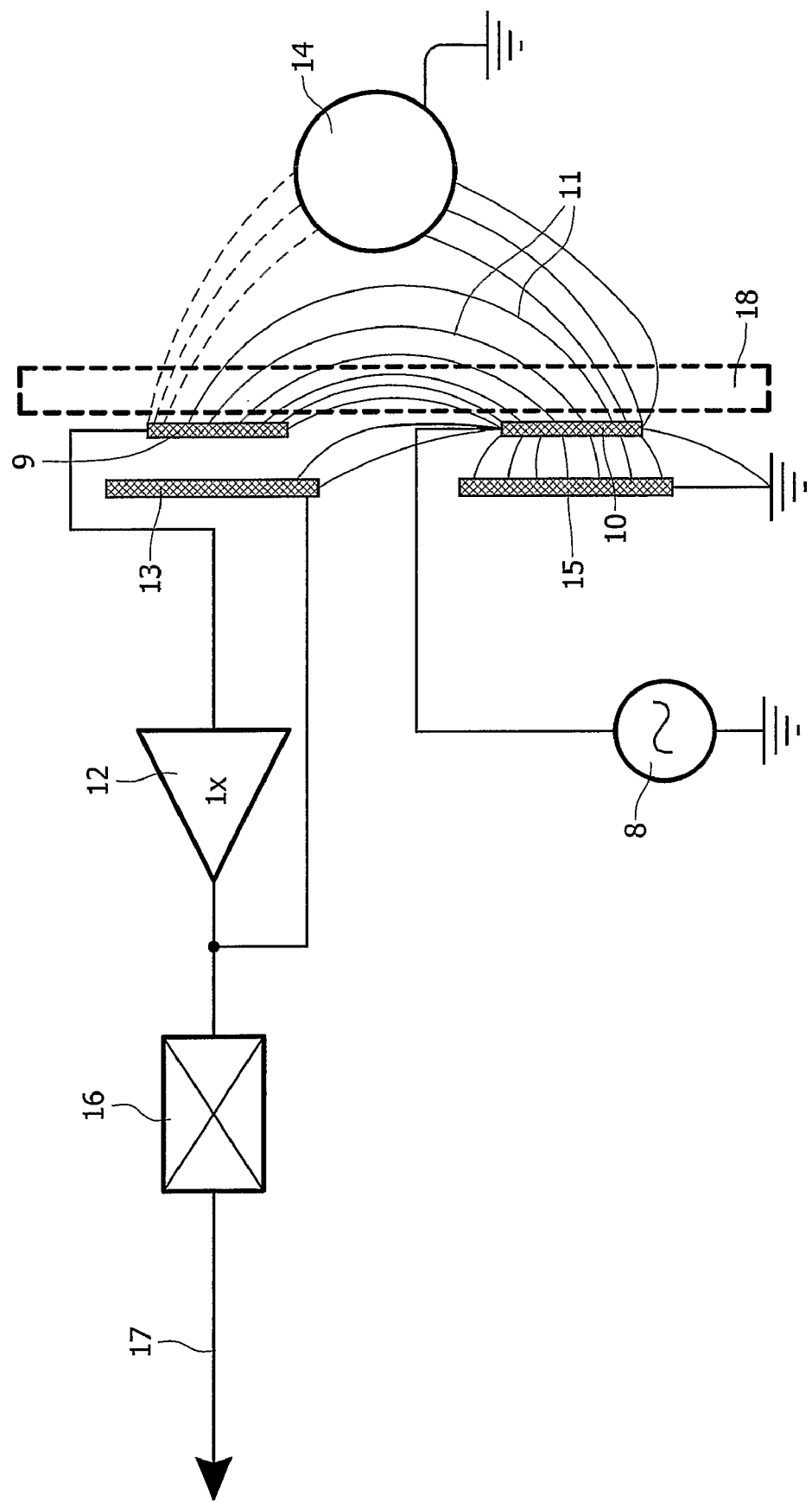
FIG. 3 is a schematic diagram illustrating the principle of construction of a capacitive proximity sensor according to the prior art.
Figure 4:
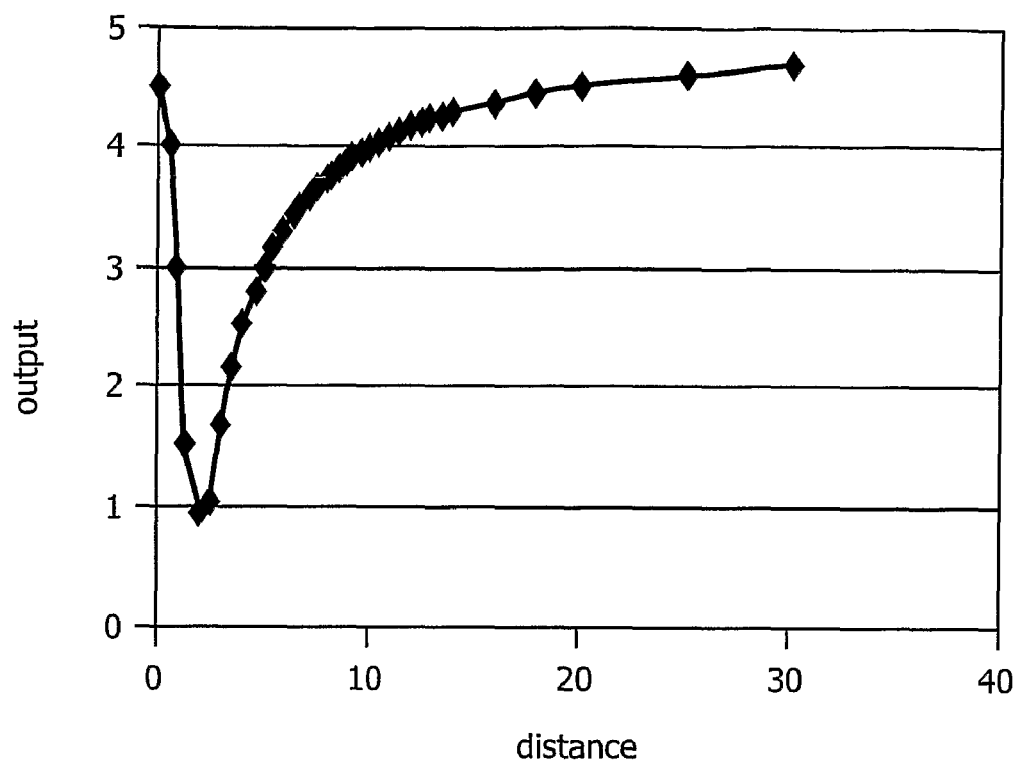
FIG. 4 is a graphical illustration of the output of a prior art proximity sensor.
Figure 6:
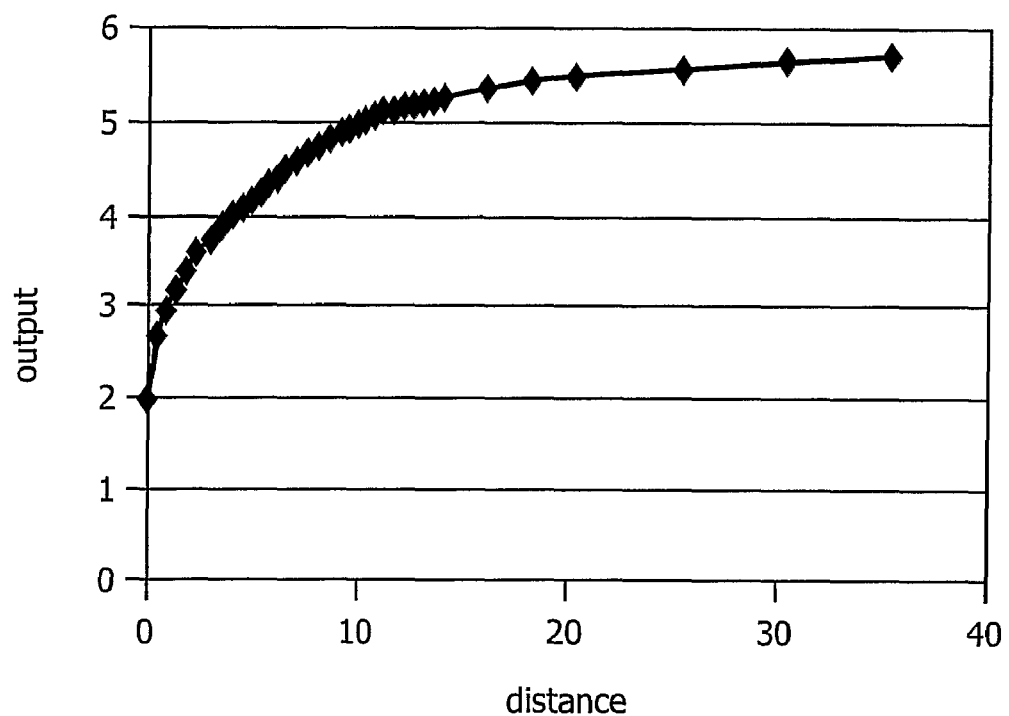
FIG. 6 is a graphical illustration of the output of the sensor of FIG. 5.

The object of the invention is achieved by blocking unwanted shortened electric field lines through the use of active guarding techniques between the emitter and receiver electrodes 104, 102. Any shortened electric field lines will fall on the second active guard electrode 103 between the receiver 102 and the emitter 104, rather than on the receiver 102, as in the prior art arrangement described with reference to FIG. 3 of the drawings. As a result, the receiver potential is no longer dependent on the shortening (changing) of electric field lines 124 caused by material changes in the sensor cover 106 with changes in humidity and temperature, nor is there the possibility that the electric field lines might be shortened by the presence of an object in the sensor proximity, as illustrated graphically in FIG. 6.

In use, the presence of an object 122 in the proximity of the sensor 100 has the effect of changing the capacitive load to input and disturbing the electric field lines 124 from the emitter 104 to the receiver 102, both of which cause a corresponding change in output potential, such that object detection can be performed by means of two mechanisms. As a result the reliability of the sensor is improved as it is able to detect the presence of more objects relative to the prior art.

The output from the sensor 100 is fed to a processing system 114, comprising the sine oscillator 101, a second signal conditioning means 116, a digital-to-analog converter 118 and an analog-to-digital converter 120.

It should be noted that the above-mentioned embodiments illustrate rather than limit the invention, and that those skilled in the art will be capable of designing many alternative embodiments without departing from the scope of the invention as defined by the appended claims. In the claims, any reference signs placed in parentheses shall not be construed as limiting the claims. The word "comprising" and "comprises", and the like, does not exclude the presence of elements or steps other than those listed in any claim or the specification as a whole. The singular reference of an element does not exclude the plural reference of such elements and vice-versa. The invention may be implemented by means of hardware comprising several distinct elements, and by means of a suitably programmed computer. In a device claim enumerating several means, several of these means may be embodied by one and the same item of hardware. The mere fact that certain measures are recited in mutually different dependent claims does not indicate that a combination of these measures cannot be used to advantage.

The invention claimed is:

1. A swing arm for an imaging system, the swing arm comprising:
    a radiation source;
    a detector adapted to receive radiation from the radiation source;
    a protective cover; and
    a sensor comprising:
        an emitter electrode disposed behind the protective cover;
        a receiver electrode disposed behind the protective cover laterally with respect to the emitter electrode,
        an oscillator coupled to the emitter electrode to cause the emitter electrode to generate an electric field that passes from the emitter electrode, through the protective cover a first time, back through the protective cover a second time, and is received by the receiver electrode, and
        an electrically driven guard electrode disposed behind the protective cover laterally between the emitter and receiver electrodes so as to prevent shortened lines of the electric field from the emitter electrode from reaching the receiver electrode,
        wherein detection of an object in proximity to the sensor is indicated by a reduction of sensor output voltage from the receiver electrode.

2. The swing arm of claim 1, wherein the sensor further comprises a second, electrically driven guard electrode disposed in parallel with respect of said receiver electrode to shield parts thereof not facing the object.

3. The swing arm of claim 2, wherein said receiver electrode is connected to the input of an amplifier, the output of which drives said first and second guard electrodes.

4. The swing arm of claim 1, wherein the gain of said amplifier is substantially unity.

5. The swing arm of claim 1, wherein a grounded shield is provided in respect of said emitter electrode to shield parts thereof not facing a potential object.

6. An imaging system, comprising:
    a robotic arm; and
    a swing arm connected to the robotic arm, the swing arm comprising:
        a radiation source;
        a detector adapted to receive radiation from the radiation source;
        a protective cover; and
        a proximity sensor, comprising:

an emitter electrode disposed behind the protective cover;

a receiver electrode disposed behind the protective cover laterally with respect to the emitter electrode, an oscillator coupled to the emitter electrode to cause the emitter electrode to generate an electric field that passes from the emitter electrode, through the protective cover a first time, back through the protective cover a second time, and is received by the receiver electrode, and an electrically driven guard electrode disposed behind the protective cover laterally between the emitter and receiver electrodes so as to prevent shortened lines of the electric field from the emitter electrode from reaching the receiver electrode, wherein detection of an object in proximity to the proximity sensor is indicated by a reduction of sensor output voltage from the receiver electrode;

motive means for moving said swing arm to a desired position relative to a subject to be imaged; and means for controlling said motive means according to the output of said proximity sensor.

7. The imaging system of claim 6, wherein the proximity sensor further comprises a second, electrically driven guard electrode disposed in parallel with respect of said receiver electrode to shield parts thereof not facing the object.

8. The imaging system of claim 7, wherein said receiver electrode is connected to the input of an amplifier, the output of which drives said first and second guard electrodes.

9. The imaging system of claim 6, wherein the gain of said amplifier is substantially unity.

10. The imaging system of claim 6, wherein a grounded shield is provided in respect of said emitter electrode, to shield parts thereof not facing a potential object.

* * * * *